United States Patent
Erman et al.

(10) Patent No.: US 7,173,146 B1
(45) Date of Patent: Feb. 6, 2007

(54) MENTHYL LACTATE PROCESS

(75) Inventors: Mark B. Erman, Atlantic Beach, FL (US); Joe W. Snow, Kingsland, GA (US)

(73) Assignee: Millennium Specialty Chemicals, Inc., Jacksonville, FL (US)

( * ) Notice: Subject to any disclaimer, the term of this patent is extended or adjusted under 35 U.S.C. 154(b) by 0 days.

(21) Appl. No.: 11/249,243

(22) Filed: Oct. 13, 2005

(51) Int. Cl.
*C07C 69/66* (2006.01)

(52) U.S. Cl. .................................... 560/188
(58) Field of Classification Search ............... 560/188
See application file for complete search history.

(56) References Cited

U.S. PATENT DOCUMENTS 5,783,725 A * 7/1998 Kuhn et al. ............... 560/188

2005/0054651 A1 3/2005 Natarajan et al. ........... 514/249

OTHER PUBLICATIONS

K. Nishiyama et al., *J. Chem. Soc., Chem. Commun.*, (1976) 101.
I. Ojima et al., *J. Org. Chem.* 42 (1977) 1671.
A. McKenzie et al., *J. Chem. Soc.* 87 (1905) 1016.
L. Horner et al., *Liebigs Ann. Chem.* (1979) 1232.

* cited by examiner

*Primary Examiner*—Thurman K. Page
*Assistant Examiner*—Lalitha Nagubandi
(74) *Attorney, Agent, or Firm*—Jonathan L. Schuchardt

(57) ABSTRACT

A simple, high-yield process for making menthyl lactate (ML) is disclosed. Menthol and lactic acid react to produce a mixture comprising menthyl lactate and one or more higher lactoyl esters of ML. Hydrolysis of the esterification mixture follows in the presence of aqueous base under conditions effective to convert the higher lactoyl esters to menthyl lactate. Coincidentally, the conditions minimize hydrolysis of menthyl lactate to menthol, thereby maximizing the overall yield of ML.

10 Claims, No Drawings

MENTHYL LACTATE PROCESS

FIELD OF THE INVENTION

The invention relates to a high-yield process for obtaining menthyl lactate by esterification and controlled hydrolysis.

BACKGROUND OF THE INVENTION

Menthyl lactate (ML), an ester of menthol and lactic acid, is a physiological cooling agent widely used in flavors, oral care, and cosmetics. Recently, ML was proposed for cancer treatment or as a diagnostic agent (see, e.g., U.S. Pat. Appl. Publ. 2005/0054651). Because ML has four chiral centers, there are sixteen possible stereoisomers. The most common ML isomer, 1, derives from l-menthol and L(+)-lactic acid:

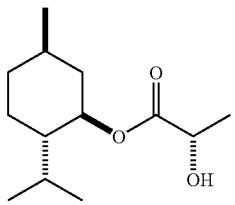

1

Few synthetic routes to ML have been reported. One general approach involves asymmetric reduction of menthyl pyruvate (see, e.g., Nishiyama et al., *J. Chem. Soc. Chem. Commun.* (1976) 101 and Ojima et al., *J. Org. Chem.* 42 (1977) 1671. This approach uses sophisticated chiral reagents and gives ML in modest chemical and optical yields.

The simplest way to make ML is direct esterification of lactic acid with menthol. Surprisingly few details about this method are available in the literature, however. A century ago, McKenzie et al. (*J. Chem. Soc.* 87 (1905) 1016) described the preparation of l-menthyl-dl-lactate by esterification from l-menthol and dl-lactic acid "by the hydrogen chloride method." This appears to involve bubbling hydrogen chloride gas into an ether solution containing l-menthol and an excess amount of dl-lactic acid, followed by washing the ether phase with aqueous sodium carbonate and water, followed by drying, concentration, and distillation. McKenzie observed changes in optical activity when optically active menthyl or bornyl esters (including ML) were hydrolyzed with alcoholic potassium hydroxide at elevated temperature to give the corresponding carboxylic acid salts. The conditions used were not effective to minimize hydrolysis of menthyl lactate; in fact, they were designed to produce menthol and lactic acid by hydrolyzing ML.

Kuhn et al. (U.S. Pat. No. 5,783,725) teach an acid-catalyzed esterification of L(+)-lactic acid and l-menthol. The recommended acids are sulfuric acid, phosphoric acid, methanesulfonic acid, p-toluenesulfonic acid, acid clays, and acidic ion-exchange resins. After a typical workup, the ML product is distilled to 97–98% purity. The reference provides few synthetic details and is silent about the yield of ML obtained.

Direct esterification is also taught by L. Horner et al. (*Liebigs Ann. Chem.* (1979) 1232). L(+)-Lactic acid and l-menthol are esterified in the presence of chloroform and a strongly acidic ion-exchange resin. After elution with chloroform through a column of alumina and solvent removal, the residue is fractionally distilled to provide a 39% yield of ML.

An improved way to make menthyl lactate is needed. A desirable process would avoid expensive reagents; instead, it would retain the convenience and simplicity of direct esterification. Ideally, the process would be simple to practice and would provide high yields of ML

SUMMARY OF THE INVENTION

We surprisingly found that the reaction of lactic acid and menthol produces not only menthyl lactate but also significant amounts of higher lactoyl esters of ML, including menthyl lactoyl lactate (MLL) and menthyl lactoyl lactoyl lactate (MLLL). The higher lactoyl esters, although previously unknown, can comprise 25% or more of a direct esterification mixture; unfortunately, the usual distillation to obtain ML sacrifices them in a high-boiling fraction that is normally discarded.

In one process of the invention, menthol and lactic acid react to produce a mixture comprising menthyl lactate and one or more higher lactoyl esters of menthyl lactate. Hydrolysis of the esterification mixture follows in the presence of aqueous base and under conditions effective to convert the higher lactoyl esters to menthyl lactate. Coincidentally, the conditions minimize hydrolysis of menthyl lactate to menthol, thereby maximizing the overall yield of ML. Another process of the invention involves controlled hydrolysis of a mixture comprising higher lactoyl esters of menthyl lactate. Each process is simple to practice and provides exceptionally high yields of ML.

DETAILED DESCRIPTION OF THE INVENTION

Menthyl lactate (ML) is produced by the direct reaction of menthol and lactic acid.

Menthol suitable for use in the invention can have any desired stereochemistry. With three chiral centers, menthol has eight possible stereoisomers. A menthol sample might have several different stereoisomers present. Examples include l-menthol, d-menthol, dl-menthol (i.e., a racemic mixture of l-menthol and d-menthol), isomers of neomenthol, isomenthol, and neoisomenthol, and mixtures thereof. l-Menthol, d-menthol, dl-menthol, and other isomers are all commercially available. Because it provides ML having excellent physiological cooling properties, l-menthol (2) is particularly preferred.

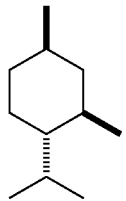

2

Lactic acid reacts with menthol to make ML. With one chiral center, lactic acid has two possible stereoisomers, L-(+)-lactic acid and D-(−)-lactic acid. Lactic acid is commonly supplied as a concentrated solution in water (e.g., 85+wt. % lactic acid). An example is HS-88 solution, a product of Purac, which contains about 88 wt. % of lactic acid in water. Suitable lactic acid for use herein includes L-(+)-lactic acid, D-(−)-lactic acid, the racemic mixture (i.e., DL-lactic acid), and mixtures thereof. Because it provides ML having excellent physiological cooling properties, L-(+)-lactic acid (3) is particularly preferred.

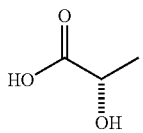

3

Direct esterification of lactic acid with menthol generally produces a mixture comprising menthyl lactate and one or more higher lactoyl esters of menthyl lactate. Although previously unknown, simply heating menthol and lactic acid together (usually in the presence of a solvent such as heptane, toluene, or the like to assist in removing water formed as a result of esterification) generates higher lactoyl esters of ML, including MLL, MLLL, and traces of even higher esters.

MLL

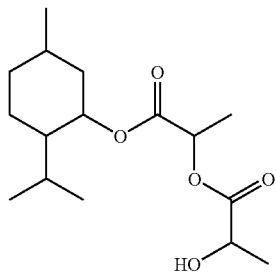

MLLL

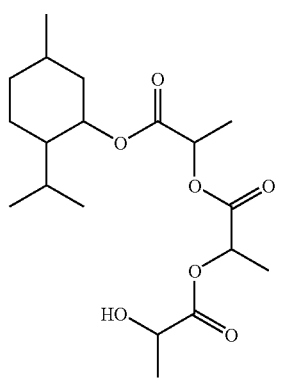

How the higher lactoyl esters form is not critical. The mechanism may involve successive formation of ML, MLL, MLLL, and so on, as additional lactic acid condenses with the lower ester. Of course, other mechanisms are possible, including initial formation of lactic acid oligomers followed by condensation with menthol, a combination of the two mechanisms described above, or some other pathway.

The process of the invention will benefit any direct esterification process for making ML that generates higher lactoyl esters of ML. Often, the reaction mixture contains unreacted menthol, menthenes, and/or cyclic dimers of lactic acid ("lactides") in addition to ML and the higher lactoyl esters of ML. As noted earlier, water of reaction is preferably removed to promote esterification; a hydrocarbon solvent and a Barrett or Dean-Stark trap are advantageously used.

The esterification is performed at any convenient temperature. Generally, the esterification proceeds over a range of temperatures that depend on whether a solvent is included, and if so, the identity and boiling point of the solvent. The temperature generally increases as the reaction approaches completion. Often, the esterification proceeds at or near the reflux temperature of the reaction mixture. When heptane is the solvent, for example, the esterification proceeds within the range of about 80° C. to about 130° C.

Preferably, no catalyst is used to promote the esterification reaction. However, a catalyst can be included. Suitable esterification catalysts are typically acids. Suitable catalysts include, for example, sulfuric acid, acidic ion-exchange resins, p-toluenesulfonic acid, alkali metal bisulfates, or the like, and mixtures thereof.

The esterified product containing ML and higher lactoyl esters can be purified, if desired, by any suitable means, including distillation, crystallization, or the like, but it is preferably used "as is" for the next step, which involves controlled hydrolysis. Gas chromatography, liquid chromatography, or other techniques are conveniently used to determine the degree of conversion of menthol to ML and higher lactoyl esters.

Hydrolysis is performed in the presence of aqueous base under conditions effective to convert the higher lactoyl esters to menthyl lactate while minimizing hydrolysis of menthyl lactate to menthol. While those skilled in the art appreciate that aqueous base is a good reagent for hydrolyzing esters, the challenge is to selectively hydrolyze principally MLL, MLLL, and higher oligomers to ML without hydrolyzing ML. This is difficult because the conditions that favor hydrolysis of the higher lactoyl esters to ML should also favor hydrolysis of ML to lactic acid and menthol.

Suitable bases are capable of deprotonating lactic acid. Preferably, they include alkali metal hydroxides (e.g., NaOH, KOH), alkaline earth metal hydroxides (e.g., $Mg(OH)_2$), alkali metal carbonates (e.g., $Na_2CO_3$, $K_2CO_3$), or the like. Alkali metal hydroxides such as sodium hydroxide, potassium hydroxide, lithium hydroxide, and cesium hydroxide, and alkali metal carbonates are preferred. Sodium hydroxide, potassium hydroxide, sodium carbonate, and potassium carbonate are readily available, inexpensive, and most preferred.

We found that by controlling hydrolysis conditions, such as the order of addition of reagents, rate of addition, nature and concentration of base, weight ratio between base and esterification product, pH, temperature, and other factors, we could selectively hydrolyze higher lactoyl esters, minimize hydrolysis of ML, and maximize the overall yield of ML. The controlled hydrolysis conditions can vary within broad ranges. For example, hydrolysis can be controlled by slowly adding the base at lower temperature, preferably dropwise, which helps to prevent increases in base concentration and pH. However, at somewhat higher temperatures, MLL hydrolysis proceeds faster—hence consuming the base faster—so pH stays lower and the addition rate can be increased (see, e.g., Examples 4–11).

A two-phase reaction mixture is desirable for regulating temperature and controlling hydrolysis, but it is not necessary. Thus, the reaction mixture preferably contains both water and an immiscible organic solvent such as heptane, toluene, or the like. Basic hydrolysis produces lactate salts, which dissolve preferentially in the aqueous phase, while the desired ML product remains in the organic phase.

Typically, the pH of the reaction mixture changes during the course of controlled hydrolysis, depending on the nature of base, addition order, rate of addition, and temperature.

The reaction is preferably performed under conditions that will not allow pH to exceed 14. Preferably, the pH is regulated within the range of about 9 to about 13.5. Usually, at pH values higher than 13.9, more ML than desirable is hydrolyzed to menthol.

The hydrolysis reaction mixture is optionally cooled using an external cold water bath or other means. For convenience, the preferred reaction temperature range is from about 5° C. to about 70° C., more preferably from about 15° C. to about 60° C. Usually, at temperatures greater than about 60° C., evaporation can occur, which may require additional equipment such as a condenser. At temperatures below about 15° C., some components may crystallize, which would usually require longer reaction times and stronger agitation. Nevertheless, good yields of ML can still be obtained even at temperatures significantly higher than 70° C. or lower than 15° C.

After the hydrolysis is reasonably complete—as conveniently shown by gas chromatography, liquid chromatography, or other suitable analytical techniques—the reaction mixture is usually neutralized, washed, dried, and concentrated. The ML product can be purified by any suitable method, including, for example, distillation, crystallization, precipitation, sublimation, or a combination thereof. Distillation is preferred. A skilled person can readily adjust one or more of the hydrolysis conditions (e.g., using a lower temperature or lower pH) in the event analysis shows that too much of the ML is being converted to menthol.

The invention contemplates a process which comprises hydrolyzing a mixture comprising one or more higher lactoyl esters of menthyl lactate in the presence of aqueous base under conditions effective to convert the higher lactoyl esters to menthyl lactate while minimizing hydrolysis of menthyl lactate to menthol. Thus, menthyl lactate need not be present prior to hydrolysis; it suffices to start with a mixture containing just the higher lactoyl esters of ML.

The process of the invention dramatically improves the yield of menthyl lactate obtained from direct esterification. As shown in Example 1 below, the yield of ML before hydrolysis (i.e., the GC yield) is about 68%. After distillation—even an efficient one—this will drop to 50% or less. The reported literature yield is only 39%. In contrast, when controlled hydrolysis follows, the yield of ML based on charged menthol soars to 91%, and most of the balance is unreacted menthol, which can be recovered and converted to ML.

The following examples merely illustrate the invention. Those skilled in the art will recognize many variations that are within the spirit of the invention and scope of the claims.

EXAMPLE 1

Preparation of l-Menthyl Lactate by Esterification and Controlled Hydrolysis

Esterification: A three-neck flask equipped with a Barrett trap, reflux condenser, thermocouple, heating mantle, and magnetic stirrer is charged with l-menthol (1440 g), L-(+)-lactic acid (2880 g of grade HS-88 from Purac, 88% lactic acid in water), and heptane (720 g). The stirred mixture is brought to reflux and water is periodically drained from the trap as it forms. The temperature of the mixture increases gradually to 128° C. after 32 h and after 854 mL of aqueous phase has been removed. The mixture is cooled to ambient temperature and analyzed by gas-liquid chromatography (GC). It contains: 5.4% of unreacted menthol, 67.7% of l-menthyl L-lactate (ML), 0.6% of lactide (cyclic dimer of lactic acid), 24.6% of l-menthyl L-lactoyl-L-lactate (MLL), and 0.4% of l-menthyl L-lactoyl-L-lactoyl-L-lactate (MLLL).

Controlled hydrolysis: The esterified product is diluted with water (4230 g) and heptane (960 g). Aqueous sodium hydroxide (809 g of 50% NaOH) is then added dropwise over 30 min. while the mixture is stirred and cooled (cold water bath) so that the temperature does not exceed 30° C. and the pH does not exceed 12.9. After the base addition, the mixture stirs for another 20 min. GC analysis shows practically complete conversion of MLL into ML. The layers are separated. The organic layer is washed with 1.5% aqueous lactic acid (1000 g) and then cohobated to remove moisture. The solvent (heptane) is stripped, and the residue is fractionally distilled under vacuum with the following results:

Fraction 1, 100 g, 94.5% menthol and 2.0% of ML.
Fraction 2, 111 g, 46.8% menthol, 51.8% ML.
Fraction 3, 1860 g, 99.5% pure ML.

Yield of ML contained in all three fractions based on charged menthol: 91%. Yield of purified ML based on reacted menthol: 98%.

EXAMPLE 2

Preparation of l-Menthyl Lactate by Sulfuric Acid-Catalyzed Esterification and Controlled Hydrolysis Esterification: The procedure of Example 1 is generally followed using 1000 g of l-menthol, 1000 g of L-(+)-lactic acid, 500 g of heptane, and 6 g of concentrated sulfuric acid. The temperature of the mixture increases gradually to 119° C. after 2 h and after 300 mL of aqueous phase has been removed. The mixture is cooled and analyzed by GC. It contains: 6.4% of unreacted menthol, 57.6% of ML, 0.4% of lactide, 32.2% of MLL, and 1.9% of MLLL.

Controlled hydrolysis: The esterified product is diluted with water (800 g) and heptane (500 mL). Aqueous sodium hydroxide (204 g of 50% NaOH) is then added dropwise over 70 min. while the mixture is stirred and cooled (cold water bath) so that the temperature does not exceed 30° C. and the pH does not exceed 13.1. The layers are separated. The organic layer is diluted with water (1350 g) and treated with more 50% aq. sodium hydroxide (150 g), which is added dropwise over 1 h in the manner described above. After the base addition, the mixture stirs for about 1 h. GC analysis shows practically complete conversion of MLL into ML. The layers are separated. The organic layer is washed with water.

The entire procedure of esterification and controlled hydrolysis is repeated. The washed organic layers are combined, the solvent (heptane) is stripped, and the residue is fractionally distilled under vacuum with the following results:

Fraction 1, 203 g, 87.1% menthol, 3.5% ML, and 6.2% menthenes.
Fraction 2, 96.8 g, 57.2% menthol, 41.6% ML.
Fraction 3, 2356 g, 99.4% pure ML.

Yield of ML contained in all three fractions based on charged menthol: 81%. Yield of purified ML based on reacted menthol: 91%.

EXAMPLE 3

Preparation of l-Menthyl Lactate by Sodium Bisulfate-Catalyzed Esterification The esterification procedure of Example 1 is generally followed using 1000 g of l-menthol, 2000 g of L-(+)-lactic acid, 500 g of heptane, and 10 g of crystalline $NaHSO_4 \cdot H_2O$. The reflux starts at about 93° C. and finishes at about 123° C. after about 581 g of the water is drained, which takes slightly under 17 h. Composition of the mixture (%, GC): menthol 3.3%, ML 48.7%, lactide 4.8%, MLL 36.5%, MLLL 5.6%. The mixture is then used in the hydrolysis experiments described below.

EXAMPLES 4–11

Controlled Hydrolysis: Normal Mode of Addition

These examples illustrate that desirable results are obtained by addition of the aqueous base to the esterification mixture at various temperatures at pH below 14.

General procedure. In a 500-mL flask equipped with a magnetic stirrer, thermocouple, and pH probe, crude ML (88.7 g, obtained as described above in Example 3) is mixed with water (89 g) and heptane (20 g). The mixture is brought to the test temperature using a thermostat. While stirring, 50% aq. NaOH (35.5 g) is then pumped gradually (0.6–3.6 hours) into the thermostatted flask, and pH is recorded periodically. After base addition, the mixture is agitated for several minutes until the GC peak corresponding to MLL drops below 1%. Results appear in Table 1.

TABLE 1

Effect of Controlled Hydrolysis on Product Composition

| Ex | Temp (° C.) | Addition time (hours) | Maximum pH[1] | Product composition, % (by GC) | | |
|---|---|---|---|---|---|---|
| | | | | Menthol | ML[2] | MLL |
| 4 | 15 | 3.6 | 13.18 | 5.95 | 93.02 | 0.73 |
| 5 | 25 | 2.9 | 12.68 | 7.25 | 92.29 | 0.21 |
| 6 | 30 | 2.9 | 12.55 | 7.13 | 92.41 | 0.21 |
| 7 | 40 | 2.8 | 12.03 | 7.08 | 92.38 | 0.28 |
| 8 | 50 | 2.2 | 11.65 | 7.50 | 92.06 | 0.18 |
| 9 | 60 | 2.0 | 12.24 | 6.27 | 92.54 | 0.90 |
| 10 | 60 | 0.8 | 12.07 | 7.82 | 91.65 | 0.18 |
| 11 | 60 | 0.6 | 12.45 | 6.78 | 92.16 | 0.56 |

[1]Maximum pH recorded during base addition
[2]Main isomer.

COMPARATIVE EXAMPLES 12–17

Reverse Addition

These examples illustrate that less desirable results are obtained when the esterification mixture is added to the aqueous base (i.e., reverse addition), with pH reaching or exceeding 14.

General Procedure. Aqueous NaOH (35.5 g of 50% solution) is charged to a 500-mL flask equipped with a magnetic stirrer, thermocouple, and pH probe. The stirred mixture is brought to the test temperature using a thermostat. In a separate flask, crude ML (88.7 g, obtained as described in Example 3) is mixed with water (89 g) and heptane (20 g). The stirred mixture is pumped over 0.6–3.6 hours into the thermostatted flask containing aqueous base. Results appear in Table 2.

TABLE 2

Effect of Reverse Addition on Product Composition

| Ex | Temp (° C.) | Addition time (hours) | Maximum pH[1] | Product composition, % (by GC) | | |
|---|---|---|---|---|---|---|
| | | | | Menthol | ML[2] | MLL |
| C12 | 15 | 3.6 | ≧14.0 | 12.96 | 82.36 | 2.74 |
| C13 | 25 | 3.0 | ≧14.0 | 18.41 | 75.57 | 5.84 |
| C14 | 30 | 2.6 | ≧14.0 | 29.51 | 62.87 | 6.49 |
| C15 | 40 | 2.7 | ≧14.0 | 38.96 | 51.71 | 6.98 |
| C16 | 50 | 2.0 | ≧14.0 | 39.04 | 51.77 | 7.49 |
| C17 | 60 | 0.6 | ≧14.0 | 36.23 | 56.84 | 5.63 |

[1]Maximum pH recorded during base addition.
[2]Main isomer.

COMPARATIVE EXAMPLE 18

This example illustrates that too much aqueous base gives a less desirable result even with normal addition.

The procedure of Example 7 is followed, except that 50 g of aqueous 50% NaOH is used instead of 35.5 g. The composition of the reaction mixture (GC) is as follows: 44.81% of l-menthol, 55.05% ML, and 0.14% of MLL.

The preceding examples are meant only as illustrations. The following claims define the invention.

We claim:

1. A process which comprises:
   (a) reacting menthol and lactic acid to produce a mixture comprising menthyl lactate and one or more higher lactoyl esters of menthyl lactate; and
   (b) hydrolyzing the mixture in the presence of aqueous base under conditions effective to convert the higher lactoyl esters to menthyl lactate while minimizing hydrolysis of menthyl lactate to menthol.

2. The process of claim 1 wherein the hydrolysis step is performed at a pH less than 14.

3. The process of claim 1 wherein the hydrolysis step is performed at a temperature within the range of about 5° C. to about 70° C.

4. The process of claim 1 wherein the menthyl lactate obtained from hydrolysis is purified by distillation, crystallization, precipitation, sublimation, or a combination thereof.

5. The process of claim 1 wherein the higher lactoyl esters comprise menthyl lactoyl lactate (MLL) and menthyl lactoyl lactoyl lactate (MLLL)

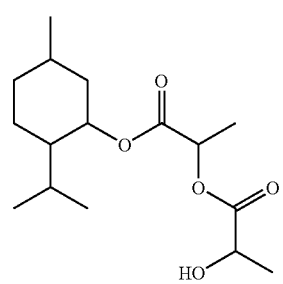

MLL

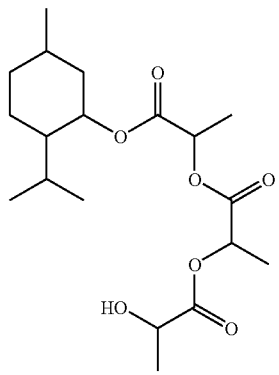 MLLL

6. A process which comprises hydrolyzing a mixture comprising one or more higher lactoyl esters of menthyl lactate in the presence of aqueous base under conditions effective to convert the higher lactoyl esters to menthyl lactate while minimizing hydrolysis of menthyl lactate to menthol.

7. The process of claim 6 performed at a pH less than 14.

8. The process of claim 6 performed at a temperature from about 5° C. to about 70° C.

9. The process of claim 6 wherein the menthyl lactate obtained from hydrolysis is purified by distillation, crystallization, precipitation, sublimation, or a combination thereof.

10. The process of claim 6 wherein the higher lactoyl esters comprise MLL and MLLL.

* * * * *

UNITED STATES PATENT AND TRADEMARK OFFICE
CERTIFICATE OF CORRECTION

PATENT NO.          : 7,173,146 B1
APPLICATION NO.  : 11/249243
DATED                    : February 6, 2007
INVENTOR(S)          : Mark B. Erman and Joe W. Snow It is certified that error appears in the above-identified patent and that said Letters Patent is hereby corrected as shown below:

Column 2, Line 52, the chemical structure should read as follows:

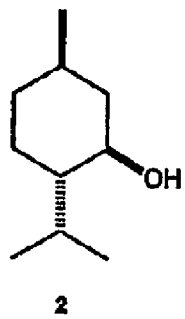

Signed and Sealed this

Tenth Day of April, 2007

JON W. DUDAS
*Director of the United States Patent and Trademark Office*